(12) United States Patent
Brady et al.

(10) Patent No.: US 7,819,893 B2
(45) Date of Patent: *Oct. 26, 2010

(54) MEDICAL DEVICE

(75) Inventors: Eamon Brady, Elphin (IE); Ronald Kelly, The Pigeons Athlone (IE)

(73) Assignee: Salviac Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 12/256,205

(22) Filed: Oct. 22, 2008

(65) Prior Publication Data

US 2009/0054924 A1     Feb. 26, 2009

Related U.S. Application Data

(60) Continuation of application No. 10/402,320, filed on Mar. 31, 2003, now Pat. No. 7,452,496, which is a division of application No. 09/887,893, filed on Jun. 25, 2001, now Pat. No. 6,565,591.

(30) Foreign Application Priority Data

Jun. 23, 2000   (WO) .................. PCT/IE00/00081
Jul. 21, 2000   (IE) ......................... 2001/0589

(51) Int. Cl.
*A61M 29/00*   (2006.01)
*B29C 49/12*   (2006.01)

(52) U.S. Cl. .............. 606/200; 606/114; 606/127; 606/194; 606/198; 264/550; 264/573

(58) Field of Classification Search .............. None
See application file for complete search history.

(56) References Cited

U.S. PATENT DOCUMENTS

| 2,854,983 A | 10/1958 | Baskin |
| 3,334,629 A | 8/1967 | Cohn |
| 3,540,431 A | 11/1970 | Mebin-Uddin |
| 3,692,029 A | 9/1972 | Adair |

(Continued)

FOREIGN PATENT DOCUMENTS

DE     3 706 077     12/1988

(Continued)

OTHER PUBLICATIONS

Co-pending U.S. Appl. No. 12/212,292, filed Sep. 17, 2008.

*Primary Examiner*—Monica A Huson
(74) *Attorney, Agent, or Firm*—Sughrue Mion, PLLC; Jonathan Feuchtwang

(57) ABSTRACT

A collapsible filter element (40) for a transcatheter embolic protection device (1). The filter element (40) comprises a collapsible filter body (41) which is movable between a collapsed stored position for movement through a vascular system and an expanded position for extension across a blood vessel such that blood passing through the blood vessel is delivered through the filter element (40). A proximal inlet portion of the filter body (41) has two inlet openings (50) sized to allow blood and embolic material enter the filter body (41), and a distal outlet portion of the filter body (41) has a plurality of small outlet openings (51) to allow through-passage of blood, but to retain embolic material within the filter body (41). The filter body (41) is of an oriented polymeric material.

23 Claims, 11 Drawing Sheets

U.S. PATENT DOCUMENTS

| | | |
|---|---|---|
| 3,730,185 A | 5/1973 | Cook et al. |
| 3,749,654 A | 7/1973 | Mikulski |
| 3,952,747 A | 4/1976 | Kimmell, Jr. |
| 4,295,464 A | 10/1981 | Shihata |
| 4,404,971 A | 9/1983 | LeVeen et al. |
| 4,423,725 A | 1/1984 | Baran et al. |
| 4,425,908 A | 1/1984 | Simon |
| 4,445,892 A | 5/1984 | Hussein et al. |
| 4,493,711 A | 1/1985 | Chin et al. |
| 4,512,762 A | 4/1985 | Spears |
| 4,585,000 A | 4/1986 | Hershenson |
| 4,610,662 A | 9/1986 | Weikl et al. |
| 4,611,594 A | 9/1986 | Grayhack et al. |
| 4,619,246 A | 10/1986 | Molgaard-Nielsen et al. |
| 4,650,466 A | 3/1987 | Luther |
| 4,723,549 A | 2/1988 | Wholey et al. |
| 4,790,812 A | 12/1988 | Hawkins, Jr. et al. |
| 4,794,928 A | 1/1989 | Kletschka |
| 4,873,978 A | 10/1989 | Ginsburg |
| 4,926,858 A | 5/1990 | Gifford, III et al. |
| 4,927,426 A | 5/1990 | Dretler |
| 5,011,488 A | 4/1991 | Ginsburg |
| 5,026,377 A | 6/1991 | Burton et al. |
| 5,053,008 A | 10/1991 | Bajaj |
| 5,108,419 A | 4/1992 | Reger et al. |
| 5,122,125 A | 6/1992 | Deuss |
| 5,178,158 A | 1/1993 | de Toledo |
| 5,192,284 A | 3/1993 | Pleatman |
| 5,324,304 A | 6/1994 | Rasmussen |
| 5,329,942 A | 7/1994 | Gunther et al. |
| 5,336,234 A | 8/1994 | Vigil et al. |
| 5,405,329 A | 4/1995 | Durand |
| 5,593,394 A | 1/1997 | Kanesaka et al. |
| 5,662,671 A | 9/1997 | Barbut et al. |
| 5,669,933 A | 9/1997 | Simon et al. |
| 5,695,519 A | 12/1997 | Summers et al. |
| 5,766,203 A | 6/1998 | Imran et al. |
| 5,769,816 A | 6/1998 | Barbut et al. |
| 5,769,871 A | 6/1998 | Mers Kelly et al. |
| 5,795,322 A | 8/1998 | Boudewijn |
| 5,800,457 A | 9/1998 | Gelbfish |
| 5,800,525 A | 9/1998 | Bachinski et al. |
| 5,814,064 A | 9/1998 | Daniels et al. |
| 5,823,992 A | 10/1998 | Salmon et al. |
| 5,827,324 A | 10/1998 | Cassell et al. |
| 5,848,964 A | 12/1998 | Samuels |
| 5,897,567 A | 4/1999 | Ressemann et al. |
| 5,910,154 A | 6/1999 | Tsugita et al. |
| 5,911,734 A | 6/1999 | Tsugita et al. |
| 5,941,869 A | 8/1999 | Patterson et al. |
| 5,954,745 A | 9/1999 | Gertler et al. |
| 5,976,172 A | 11/1999 | Homsma et al. |
| 5,993,469 A | 11/1999 | McKenzie et al. |
| 6,001,118 A | 12/1999 | Daniel et al. |
| 6,027,520 A | 2/2000 | Tsugita et al. |
| 6,042,598 A | 3/2000 | Tsugita et al. |
| 6,053,832 A | 4/2000 | Saito |
| 6,053,932 A | 4/2000 | Daniel et al. |
| 6,129,739 A | 10/2000 | Khosravi |
| 6,132,458 A | 10/2000 | Staehle et al. |
| 6,152,946 A | 11/2000 | Broome et al. |
| 6,171,327 B1 | 1/2001 | Daniel et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,245,012 B1 | 6/2001 | Kleshinski |
| 6,245,089 B1 | 6/2001 | Daniel et al. |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,319,242 B1 | 11/2001 | Patterson et al. |
| 6,325,815 B1 | 12/2001 | Kusleika et al. |
| 6,336,934 B1 | 1/2002 | Gilson et al. |
| 6,346,116 B1 | 2/2002 | Brooks et al. |
| 6,361,546 B1 | 3/2002 | Khosravi |
| 6,620,182 B1 | 9/2003 | Khosravi et al. |
| 6,695,813 B1 | 2/2004 | Boyle et al. |
| 6,726,701 B2 | 4/2004 | Gilson et al. |
| 2001/0012951 A1 | 8/2001 | Bates et al. |
| 2001/0020175 A1 | 9/2001 | Yassour et al. |
| 2001/0041908 A1 | 11/2001 | Levinson et al. |
| 2001/0044632 A1 | 11/2001 | Daniel et al. |
| 2002/0002384 A1 | 1/2002 | Gilson et al. |
| 2002/0004667 A1 | 1/2002 | Adams et al. |
| 2002/0022858 A1 | 2/2002 | Demond et al. |
| 2002/0022860 A1 | 2/2002 | Borillo et al. |
| 2002/0026211 A1 | 2/2002 | Khosravi et al. |
| 2002/0026213 A1 | 2/2002 | Gilson et al. |
| 2002/0049467 A1 | 4/2002 | Gilson et al. |
| 2002/0052626 A1 | 5/2002 | Gilson et al. |
| 2002/0058911 A1 | 5/2002 | Gilson et al. |
| 2002/0058963 A1 | 5/2002 | Vale et al. |
| 2002/0062133 A1 | 5/2002 | Gilson et al. |
| 2002/0107541 A1 | 8/2002 | Vale et al. |

FOREIGN PATENT DOCUMENTS

| | | |
|---|---|---|
| EP | 0256683 | 2/1988 |
| EP | 0533511 | 3/1993 |
| EP | 0743046 | 11/1996 |
| EP | 0791340 | 8/1997 |
| EP | 0827756 | 3/1998 |
| EP | 1123688 | 8/2001 |
| EP | 1127556 | 8/2001 |
| EP | 1149566 | 10/2001 |
| FR | 2 580 504 | 10/1986 |
| FR | 2 616 666 | 12/1988 |
| FR | 2 768 326 | 3/1989 |
| GB | 2020557 | 11/1979 |
| GB | 2200848 | 8/1998 |
| WO | 88/09683 | 12/1988 |
| WO | 89/07422 | 8/1989 |
| WO | 92/24946 | 11/1994 |
| WO | 95/32454 | 12/1995 |
| WO | 95/34339 | 12/1995 |
| WO | 96/01591 | 1/1996 |
| WO | 96/39998 | 12/1996 |
| WO | 97/03810 | 2/1997 |
| WO | 97/17021 | 5/1997 |
| WO | 97/17914 | 5/1997 |
| WO | 97/42879 | 11/1997 |
| WO | 98/24377 | 6/1998 |
| WO | 98/30265 | 7/1998 |
| WO | 98/33443 | 8/1998 |
| WO | 98/38920 | 9/1998 |
| WO | 98/39053 | 9/1998 |
| WO | 98/46297 | 10/1998 |
| WO | 98/49952 | 11/1998 |
| WO | 98/50103 | 11/1998 |
| WO | 98/51237 | 11/1998 |
| WO | 99/16382 | 4/1999 |
| WO | 99/20335 | 4/1999 |
| WO | 99/23976 | 5/1999 |
| WO | 99/25252 | 5/1999 |
| WO | 99/44510 | 9/1999 |
| WO | 99/44542 | 9/1999 |
| WO | 99/51167 | 10/1999 |
| WO | 00/16705 | 3/2000 |
| WO | 00/44428 | 8/2000 |
| WO | 00/49970 | 8/2000 |
| WO | 00/56390 | 9/2000 |
| WO | 00/67664 | 11/2000 |
| WO | 00/67665 | 11/2000 |

| | | | | | | |
|---|---|---|---|---|---|---|
| WO | 00/67666 | 11/2000 | | WO | 01/43662 | 6/2001 |
| WO | 00/67667 | 11/2000 | | WO | 01/45590 | 6/2001 |
| WO | 00/67668 | 11/2000 | | WO | 01/45591 | 6/2001 |
| WO | 00/67669 | 11/2000 | | WO | 01/45592 | 6/2001 |
| WO | 00/67670 | 11/2000 | | WO | 01/49208 | 7/2001 |
| WO | 00/67671 | 11/2000 | | WO | 01/49209 | 7/2001 |
| WO | 00/67829 | 11/2000 | | WO | 01/49215 | 7/2001 |
| WO | 01/05329 | 1/2001 | | WO | 01/50982 | 7/2001 |
| WO | 01/08742 | 2/2001 | | WO | 01/52768 | 7/2001 |
| WO | 01/08743 | 2/2001 | | WO | 01/72205 | 10/2001 |
| WO | 01/12082 | 2/2001 | | WO | 01/80776 | 11/2001 |
| WO | 01/21100 | 3/2001 | | WO | 01/80777 | 11/2001 |
| WO | 01/35857 | 5/2001 | | | | |

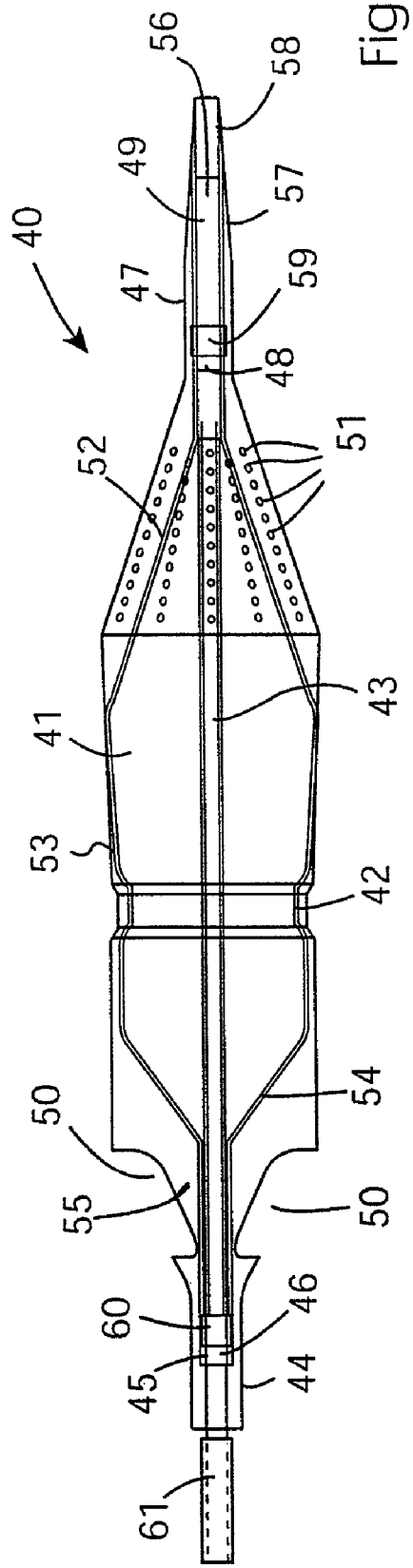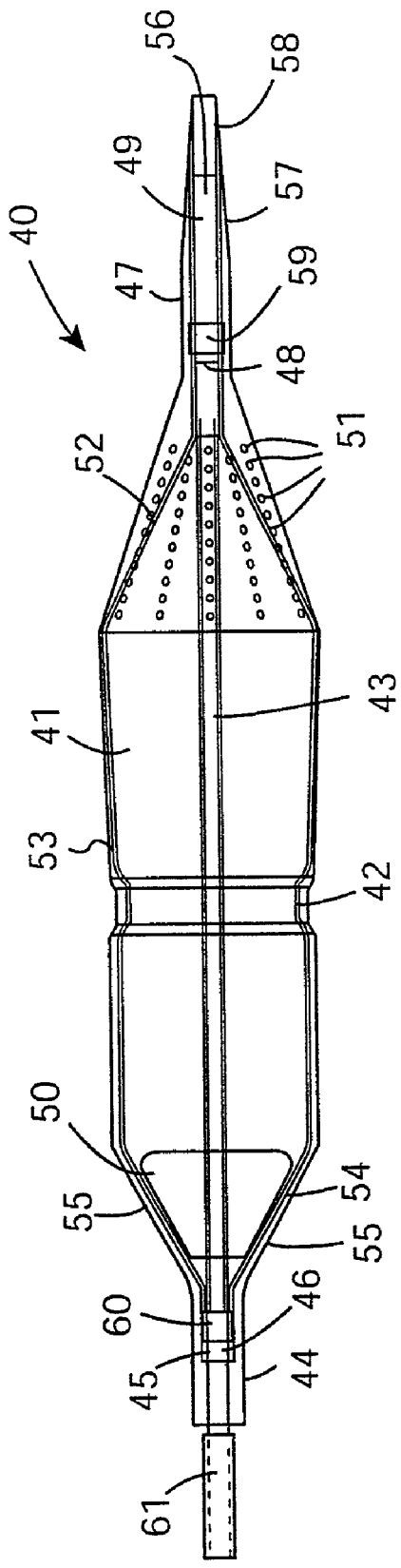

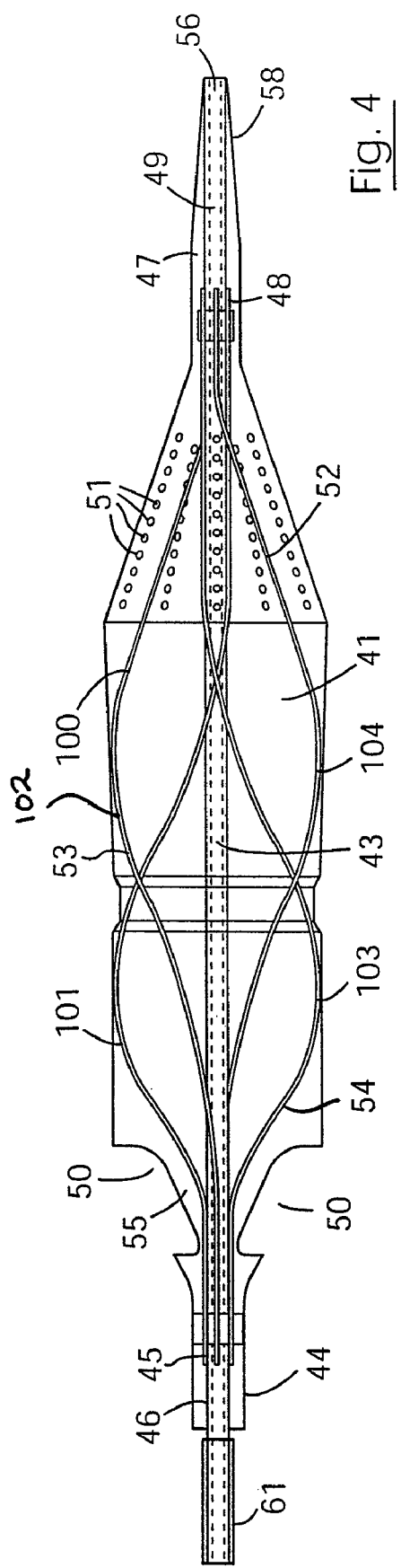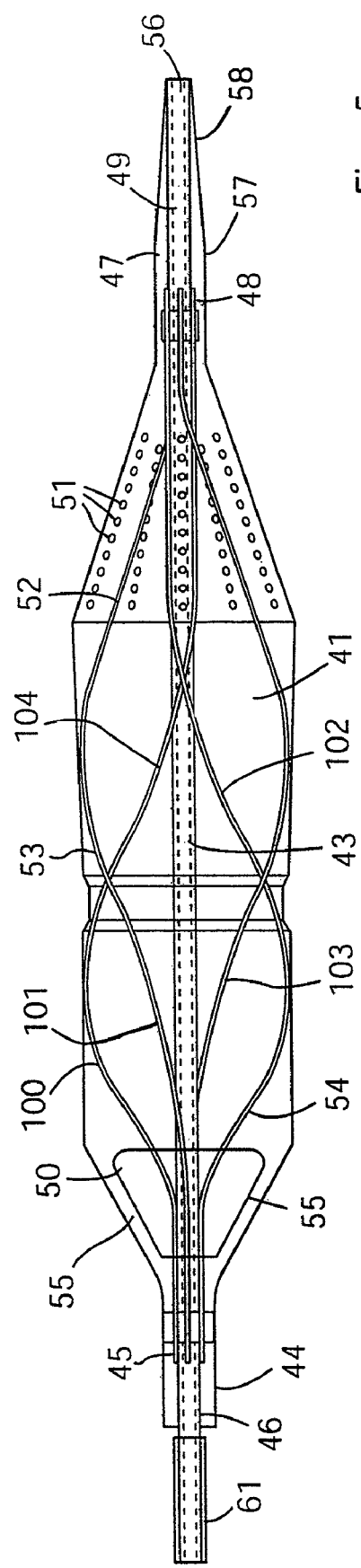

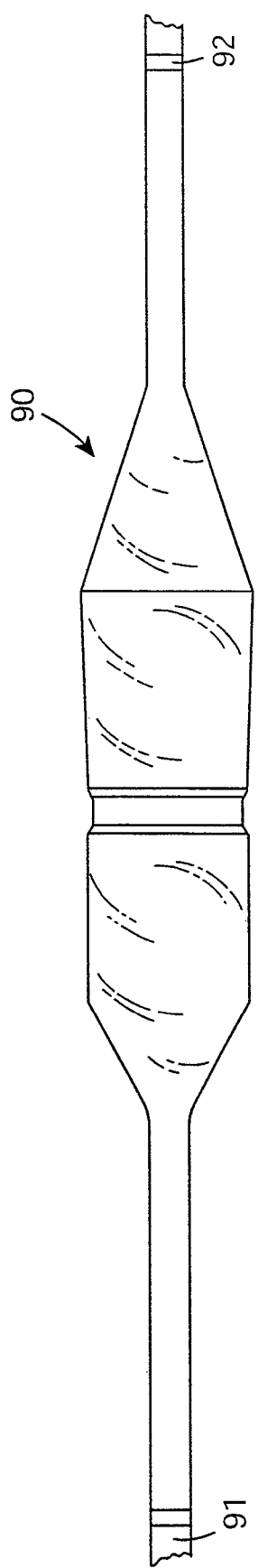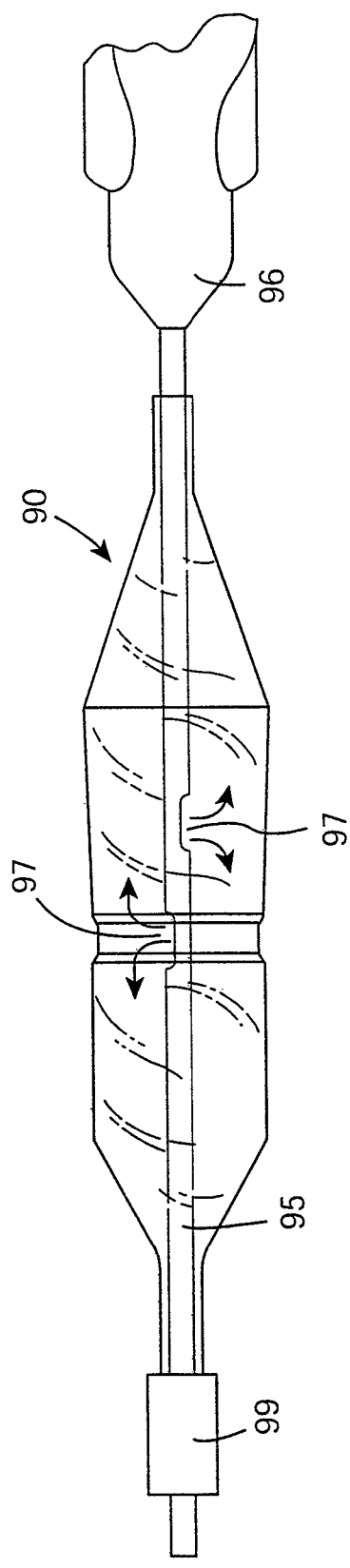

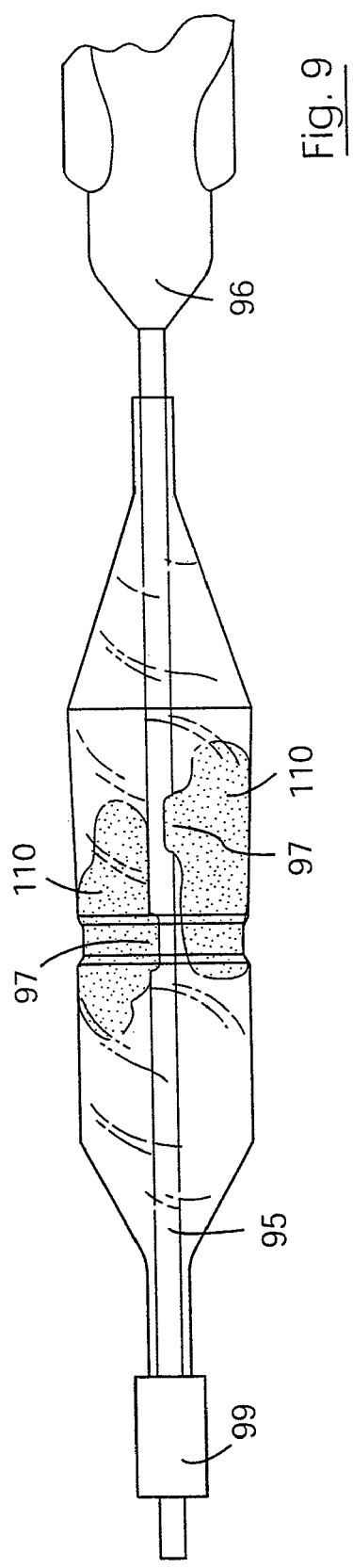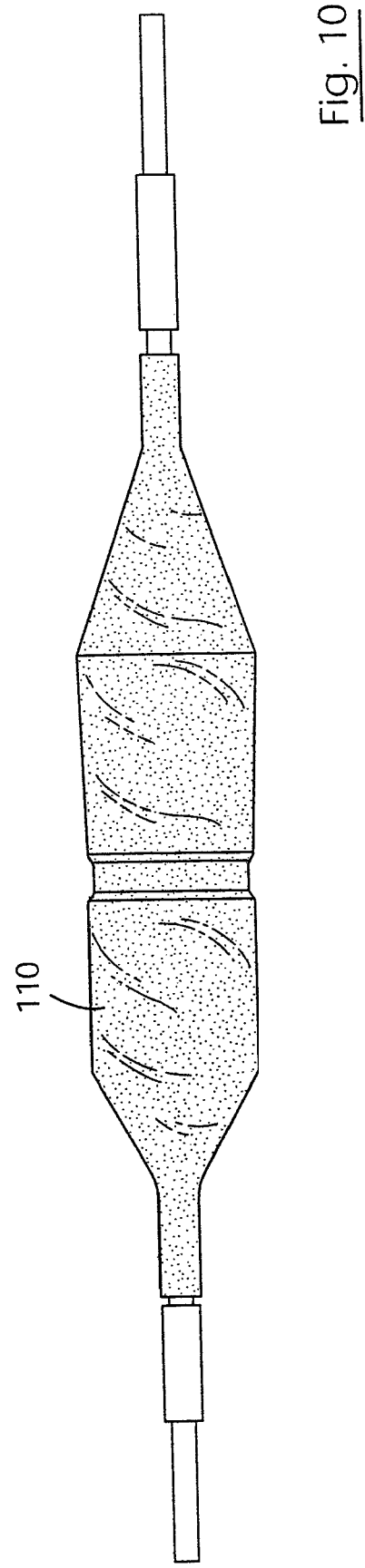

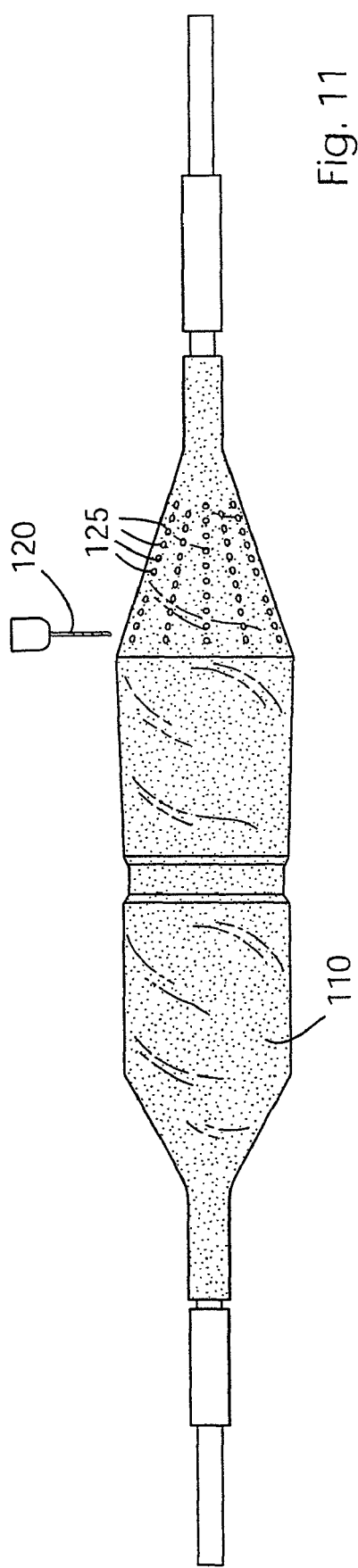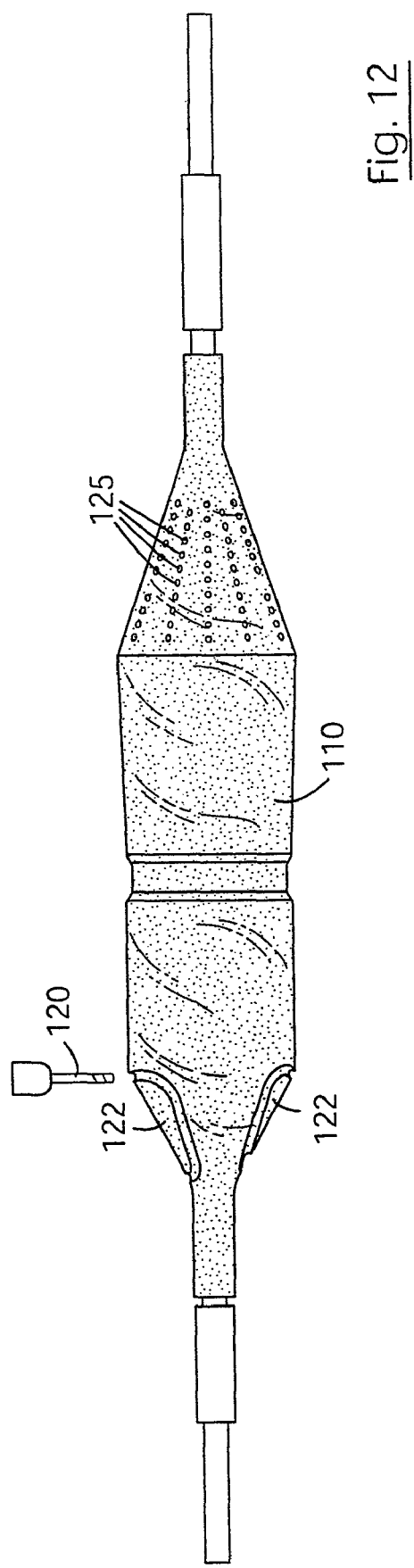

MEDICAL DEVICE

CROSS REFERENCE TO RELATED APPLICATIONS

This is a continuation application of application Ser. No. 10/402,320 filed Mar. 31, 2003, now U.S. Pat. No. 7,452,496, which is a divisional of application Ser. No. 09/887,893, filed Jun. 25, 2001, now U.S. Pat. No. 6,565,591, the above-noted applications incorporated herein by reference in their entirety.

This invention relates to a filter element for a transcatheter embolic protection device.

INTRODUCTION

The invention is particularly concerned with filter elements for transcatheter embolic protection devices of the type described in our WO-A-9923976. One type of such embolic filter comprises a filter body mounted on an associated collapsible support frame which can be collapsed against the guide wire by means of a catheter for deployment of the filter through a patient's vascular system. Upon retraction of the catheter the support frame and filter body expand outwardly from the guidewire across a blood vessel within which the filter is positioned to filter blood flowing through the blood vessel.

A practical problem that arises with filter elements of such embolic protection devices is that they should be able to accommodate blood vessels of different diameter as it would be impractical to manufacture a large range of filters each of different size to accommodate all possible diameters of blood vessel. To provide flexibility and accommodate a range of vessel sizes with a given size of filter a relatively soft and elastic filter body material can be used. It is, however, important that the filter when deployed maintains its shape during use and to prevent distortion or collapsing of the filter body in use. Because of this and also the need for adequate strength in the body material, the walls of the filter body tend to be relatively thick. This presents a problem in that the filter then has a relatively large crossing profile when in the collapsed delivery position, which is undesirable.

The present invention is directed towards overcoming these and other problems.

STATEMENTS OF INVENTION

According to the invention there is provided a collapsible filter element for a transcatheter embolic protection device, the filter element comprising:
- a collapsible filter body which is movable between a collapsed stored position for movement through a vascular system and an expanded position for extension across a blood vessel such that blood passing through the blood vessel is delivered through the filter element;
- a proximal inlet portion of the filter body having one or more inlet openings sized to allow blood and embolic material enter the filter body;
- a distal outlet portion of the filter body having a plurality of outlet openings to allow through-passage of blood, but to retain embolic material within the filter body;
- the filter body being of an oriented polymeric material.

In one embodiment of the invention the filter element comprises a collapsible support frame, the support frame being movable between a collapsed position for movement through the vascular system and an extended outwardly projecting position to support the filter body in the expanded position.

Preferably the filter body is independent of the support frame. Ideally the filter body comprises a membrane.

In one case the filter body has a stored axial orientation in excess of 15%. Preferably the filter body has a stored axial orientation in excess of 20%. Most preferably the filter body has a stored axial orientation in excess of 30%. Ideally the filter body has a stored axial orientation in excess of 40%.

In a preferred embodiment the material is biaxially oriented.

The filter body may have a stored biaxial orientation in excess of 30%. Preferably the filter body has a stored biaxial orientation in excess of 60%. Most preferably the filter body has a stored biaxial orientation in excess of 80%. Ideally the filter body has a stored biaxial orientation in excess of 100%.

In another embodiment of the invention the ultimate tensile strength of the oriented polymeric material of the filter body is at least 15,000 psi (103.425 MPa). Preferably the ultimate tensile strength is at least 25,000 psi (172.375 MPa). Most preferably the ultimate tensile strength is at least 35,000 psi (241.325 MPa). Ideally the ultimate tensile strength is at least 40,000 psi (275.8 MPa).

The material of the filter body may be of polyester or polyamide. The material of the filter body is preferably of polyester.

In one embodiment the material of the filter body is selected from polyethyleneterephthalate (PET), polybutyleneterephthalate (PBT) and polynapthylterephthalate (PNT). The material of the filter body is preferably of PET.

In another embodiment the material of the filter body is of polyamide.

In one case the material of the filter body is an elastomer. Preferably the material of the filter body is a polyurethane.

In a preferred embodiment of the invention the polymeric material of the filter body is oriented at a temperature below the glass transition temperature of the material.

The material of the filter body may be oriented by stretch blow moulding.

Desirably the filter body comprises a proximal body section, a distal body section and an intermediate body section interconnecting the proximal and distal body sections.

In one embodiment of the invention the frame comprises a plurality of engagement segments, the engagement segments being spaced-apart longitudinally and transversely when the filter is in the deployed expanded configuration to urge the filter body into apposition with the vessel wall. The engagement segments preferably define at least one at least partially substantially helical engagement track.

According to another aspect the invention provides a method for manufacturing a filter body for a transcatheter embolic protection device comprising forming a filter body of oriented polymeric material.

The filter body may be formed by applying an axial stretching force to a hollow body of polymeric material.

The filter body may be formed by applying a circumferential force to a hollow body of polymeric material.

Ideally the method comprises stretch blow moulding a polymeric material.

In one embodiment of the invention the polymeric material is oriented at a temperature above the glass transition temperature of the material or one of its phases, and below the melting temperature of the material.

The method preferably comprises the step of conditioning the formed filter body. Ideally the conditioning is carried out at a temperature in the region of the crystallization temperature of the material.

Desirably the method comprises providing inlet and outlet holes in the body of oriented material. Ideally the holes are provided by
filling the formed body with a filler material;
machining holes in the filled body; and
removing the filler material.

In one case the filler material is a soluble material, such as polyethylene glycol.

BRIEF DESCRIPTION OF THE DRAWINGS

The invention will be more clearly understood from the following description thereof given by way of example only with reference to the accompanying drawings in which:

FIG. 2 is a side partially cross sectional view of the embolic protection device of FIG. 1;

FIG. 3 is a plan view of the device of FIG. 2;

FIG. 4 is a side, partially cross sectional view of another embolic protection device according to the invention;

FIG. 5 is a plan view of the device of FIG. 4;

FIG. 7 is a side view of a blank used to form a filter body according to the invention;

FIGS. 8 to 10 are views illustrating filling of the blank of FIG. 7;

FIGS. 11 and 12 are views illustrating drilling of the filled blank;

DETAILED DESCRIPTION

Figure 1:
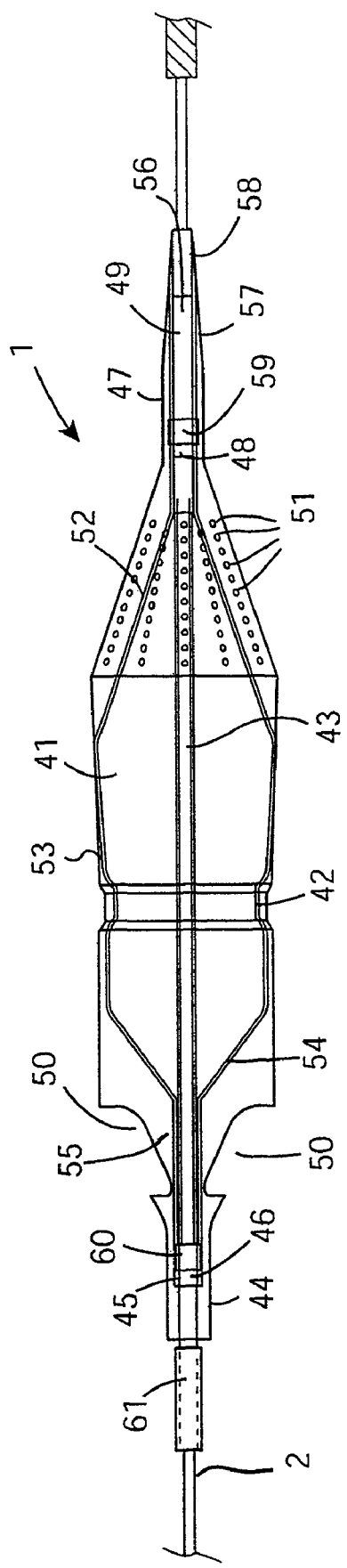
FIG. 1 is partially sectioned devotional view of an embolic protection device according to the invention in use.

Referring to FIGS. 1 to 3, an embolic protection device I comprises a collapsible filter element 40 for delivery through a vascular system of a patient and deployment at a desired location in the vascular system. An elongate sleeve 43 is slidable on a guidewire 2. The collapsible filter element 40 is mounted on the sleeve 43 and the filter element 40 is movable between a collapsed stored position against the sleeve 43 and an expanded position as illustrated extended outwardly of the sleeve 43 for deployment in a blood vessel.

The filter element 90 comprises a collapsible filter body 41 and a frame 42 mounted to the elongate sleeve 43. A proximal end 44 of the filter body 41 and a proximal end 45 of the frame 42 are both fixedly attached to a proximal end 96 of the sleeve 43, in this case by means of an adhesive bond. A distal end 47 of the filter body 41 and a distal end 48 of the frame 42 are free to slide over a distal end 49 of the sleeve 43.

The filter body 41 has a proximal inlet end and a distal outlet end. The inlet end of the filter body 41 has one or more, in this case two, large inlet openings 50, and the outlet end has a plurality of, in this case approximately three hundred, small outlet openings 51 sized to allow through passage of blood but to retain undesired embolic material within the filter body 41.

The filter support frame 42 is movable between a collapsed position for movement of the filter element 40 through a vascular system and an extended outwardly projecting position to support the filter body 41 in an expanded position. The frame 42 has a distal section 52, an intermediate section 53 for urging the filter body 41 in the expanded position into apposition with a vascular vessel wall, and a proximal section 54 extending proximally and radially inwardly of the intermediate section 53.

At least part of the proximal section 54 of the frame 42 is spaced distally of the inlet openings 50 in the filter body 41 to accommodate inflow of embolic material through the inlets 50 and into the expanded filter body 41.

The frame 42 is preferably of a shape memory material, such as Nitinol, or of a superelastic material, and may have a plating of gold or other dense material around the Nitinol. The frame elements facilitate movement of the frame 42 between the collapsed position and the extended outwardly projecting position. The frame 42 is electropolished.

The sleeve 43 defines a lumen 56 extending therethrough for movement over the guidewire 2. The distal end 499 of the sleeve 43 is engageable with a stop such as a stop on the guidewire 2. The sleeve 43 is typically of polyimide.

The sleeve 43 acts as a barrier between the lumen 56 through which a guidewire may be exchanged, and the internal annular volume of the filter body 41 within which embolic material is retained. In particular, the proximal end 46 of the sleeve 43 is proximal of the inlets 50, and the distal end 49 of the sleeve 43 is distal of the small outlets 51. This ensures that all blood flows into the filter body 41 through the inlets 50, through the filter body 41 and out of the filter body 41 through the small outlets 51 which are sized to retain undesired embolic material within the filter body 41. The sleeve 43 prevents escape of any embolic material from the filter body 41 into the lumen 56, for example, during exchange of medical devices over a guidewire received within the lumen 56, or during retrieval of the filter element 40.

A guide olive 57 is provided for atraumatic delivery of the filter element 40 through a vascular system, the guide olive 57 forms an extension of the distal end 47 of the filter body 41 and tapers distally inwardly for a smooth transition profile.

Two gold marker bands 59, 60 are provided mounted to the sleeve 43. One marker band 59 is fixedly attached to the olive 57 and one marker band 60 is fixedly attached to the proximal end 45 of the frame 42. The marker bands 59, 60 assist in visualization of the filter element 40 during an interventional procedure.

A transition element 61 is fixedly mounted to the proximal end 46 of the sleeve 43, in this case by means of an adhesive bond. The transition element 61 is sized to fit the lumen of a delivery catheter to provide a smooth stiffness transition and prevent kinking.

The sub assembly of a support frame 42 and filter body 41 is loaded into a delivery catheter. On deployment, the support arms are freed to expand and the filter body 41 opposes the vessel wall.

When the filter element 40 has been deployed in a blood vessel, the catheter can be removed leaving a bare guidewire proximal to the filter 40 for use with known devices such as balloon catheter and stent devices upstream of the filter 40.

For retrieval, the filter 40 is collapsed and retrieved into a retrieval catheter. The guidewire may be left in place for further catheter advancement or may be withdrawn with or subsequent to the withdrawal of the retrieval catheter.

Figure 6:
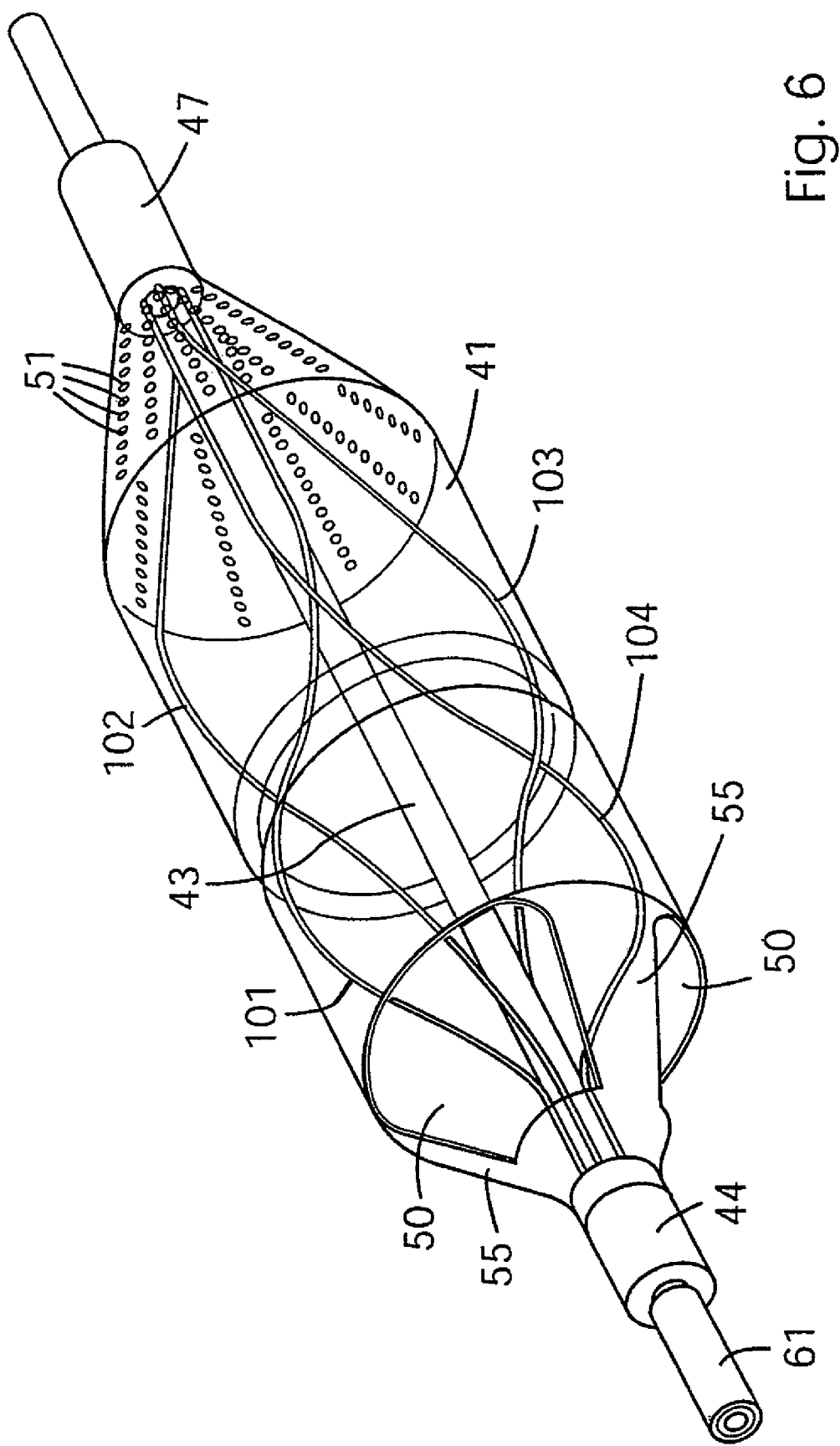
FIG. 6 is a perspective view of the device of FIGS. 4 and 5.
Figure 13:
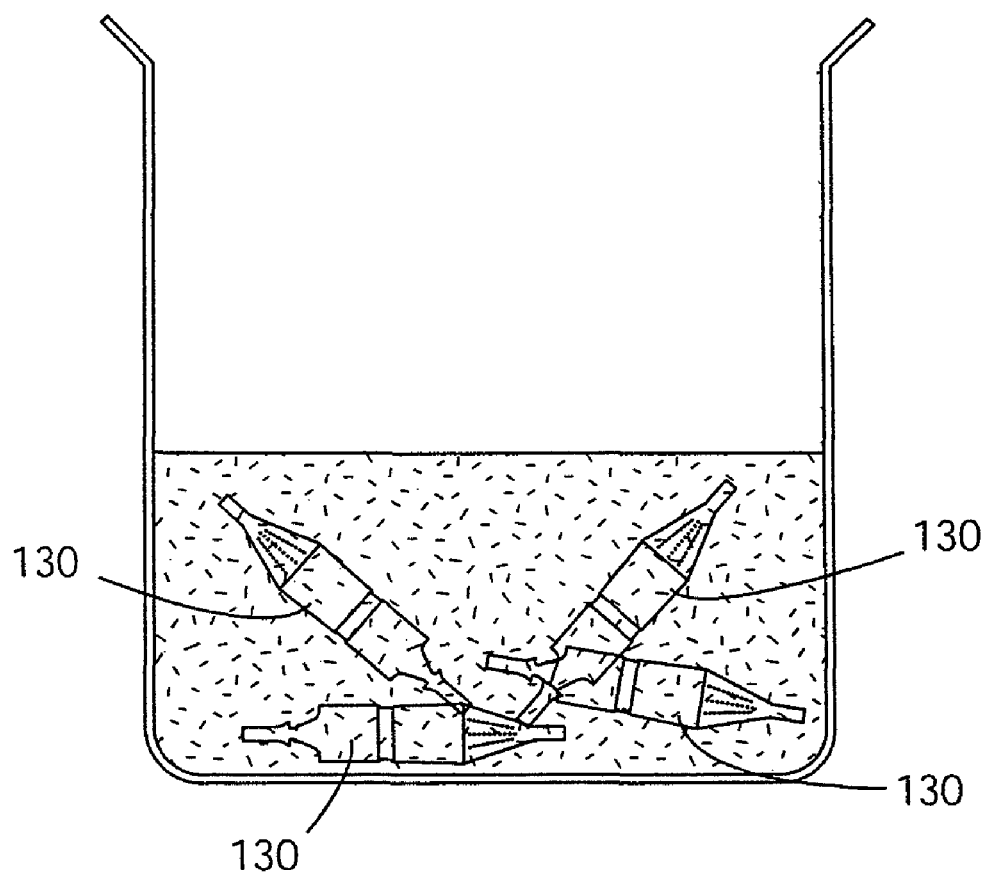
FIG. 13 is a view illustrating the removal of the filling.

Referring to FIGS. 4 to 6 there is illustrated an alternative construction of filter which is similar to that described with reference to FIGS. 1 to 3 and like parts are assigned the same reference numerals. In this case the support frame 100 comprises four support arms 101, 102, 103, 104 each of which is of at least partially of helical shape and different engagement segments of the arms are spaced-apart longitudinally and transversely when the filter is in the deployed expanded configuration illustrated. The support frame 100 is independent of the filter body 41 and provides excellent apposition with reduced loading forces. Various similar support frames are described in our WO 00/67669A, the entire contents of which are incorporated herein by reference.

According to the invention the cuter filter body 110 is of a biocompatible oriented polymeric material. The preferred materials of the invention are thermoplastic polymers. Preferably the materials have an excellent ability to store orientations, and have high strength and are flexible. Ideally the material is of the polyamide, polyurethane, polyether-amide or polyester families. Within these families materials with high ultimate tensile strength and a good ability to store induced molecular orientations at room and body temperature are preferred.

The high strength polyesters are the preferred materials of the invention. PET and PBT are the preferred polyesters. PET is the most preferred material. The grade of PET selected will depend on the level of orientation required. As the molecular structure of PET is consistent the most important difference between different grades is the molecular weight. High molecular weights are favored where the stretch ratios are low. Lower molecular weights are preferred where the stretch ratios are high.

PET is preferred because it has a high ultimate tensile strength in its isotropic state (12,000 psi), its ability to store orientations and the amplification of its strength properties in the oriented state. PET has a high glass transition temperature ($T_g$) (approx. 65° C.) and this is advantageous in that it ensures that orientations are stored at body temperature. PET is also the preferred material because it has good flexibility in thin walled configurations. A number of suppliers provide grades of PET suitable to form membranes of this invention. The preferred grades are unreinforced homopolymer grades. A preferred grade of PET is supplied by RTP Company under the name RTP 1100 Polyethylene Terephthalate. The material has an ultimate tensile strength of 10,000 psi. A preferred grade of PET is supplied by DSM under the trade name Eralyte®. This grade is the most preferred material of the invention due to its very high ultimate tensile strength of 12,300 psi.

PBT can also be used for the manufacture of membranes per this invention. PBT has an isotropic ultimate tensile strength in the region of 56 MPa. It has a similar structure to PET except that the polymethylene sequence is longer. It has a lower $T_g$ than PET of approximately 22-43° C. Commercial PBT materials are manufactured by BASF under the trade name Ultradur® and supplied by Albis Corp.

Nylons are also an excellent family of material from which to manufacture the membranes of this invention. The nylon materials possess high tensile strength and have an excellent ability to store orientation. Unlike PET which has a high $T_g$, Nylons have a $T_g$ lower than room temperature. Polyamides however are highly crystalline and it is the stability of the crystalline structure that allows Nylons to store orientations. The most important Nylons include Nylon 6, Nylon 6,6, Nylon 6,10, Nylon 6,12, Nylon 11 and Nylon 12.

Nylon 11 and Nylon 12 are the preferred Nylon materials. These materials are preferred as they are easier to process and have good resistance to moisture in vivo. Nylon 6 and Nylon 6,6 are difficult to process due to their sharp melting transition and their hygroscopic properties. Moisture acts as a plasticizer with these materials and this makes the induced orientations unstable and the membrane will shrink over time. These problems are overcome when Nylon 11 and Nylon 12 are employed. Nylon 11 has an ultimate tensile strength of approximately 52 MPa. Nylon 12 has an ultimate tensile strength of approximately 54 MPa. Suitable commercial grades of Nylon 11 are supplied by Elf Atochem under the Rilsan® trade name. Suitable grades include Rilsan® BESHV Nylon 11. Nylon 11 grades are also available from compounding companies such as RTP Company under the name RTP Nylon-11. Suitable commercial grades of Nylon 12 are supplied by Elf Atochem under the trade name Rislan® AESN nylon 12.

The PEBA family is also a family of material from which to manufacture the membranes of this invention. PEEA materials are a family of copolymers and are manufactured by the block copolymerization of polyether and polyamide. The PEBA range of materials is supplied by Elf Atochem under the trade name PEBAX® and by Creanova under the trade name VESTAMID®. Suitable grades of PEBA have hardness values in excess of 55 D. The preferred materials in this family are the 65 D and 75 D grades.

The PEBA family is a preferred family of materials per this invention. The polyurethane family is a more preferred family. Nylon 11 and Nylon 12 are even more preferred and PET is the most preferred material of the invention. PET is the most preferred material of the invention because it has a very high isotropic tensile strength, it has excellent ability to store orientations, stored orientations are highly stable at body temperature, and the amplification of PET's strength properties associated with the orientation process is most significant. The use of oriented PET allows membrane thicknesses to be reduced by up to 75% relative to isotropic PET.

The membranes utilized in the invention are made from a material that facilitates the storage of high levels of orientation but is still relatively flexible. Materials that are efficient at storing orientation at body temperature are particularly desirable. It is not so much the hardness of the material that is important as the forces the material will exert on the surface of the vessel. Relatively stiff materials when processed to very thin membrane configurations apply very little forces to the vessel and are thus atraumatic to the vessel. One ratio that is important is the ratio of the material hardness and its ultimate properties. It is also possible to characterize the material based on a flexural modulus and/or tensile modulus. This invention provides materials and processes that provide unique combinations of these desirable properties for use as filter membranes. The storage of orientation allows soft materials to be used and still achieves high strengths. It also allows these materials to be manufactured into very thin walled and thus low profile systems. These are very desirable features for filter membranes.

It is particularly preferred that the filter membrane be of an oriented polyester which are a particularly preferred class of high strength materials. PET is particularly preferred as it has ultimate tensile strength values in the region of 80 Mpa. In the invention these materials are converted into a membrane configuration and simultaneously high levels of orientation are induced into the materials. The resulting membranes will have ultimate strength values which are from 130% to in excess of 200% to in excess of 300% of the materials isotropic strength value.

Orientation is achieved by stretching the material during the forming process. The stretching thins out the membrane while orienting the molecules in the direction of stretch. If the stretch is axial then the membrane will be oriented in the axial direction. If the stretch is applied on two axes then the membrane will be bi-axially oriented.

Orientation in the axial direction is particularly desirable in the membranes of this invention. High level of axial orientations allows the manufacture of membranes with high axial strengths. As the membranes of this invention are stressed primarily in the axial direction in use the anisotropy of strength properties is a particularly advantageous feature. The process of the invention is designed to maintain high levels of axial orientation. Maximizing the level of stretch in the axial direction and maximizing the ratio of axial to circumferential stretching helps to achieve this.

Starting with an extrusion tubing whose diameter is greater than the final profile of the device is a novel strategy for achieving a low profile. However the larger the starting diameter of the tubing the smaller the circumferential stretching required. This allows the ratio of axial to circumferential stretch to be maximized which allows the generation of high axial strengths, which allows very thin walled membranes to be used.

The diameter of the necks may be reduced in a swaging operation, by bonding while the outer diameter is constrained or by slitting the necks and recombining at a smaller diameter. Alternatively the necks may be post formed to a smaller diameter.

The use of orientation allows the filter membrane to be made from a soft material and with a thin wall thickness. The ability to make very thin membranes provides the additional benefit that the ratio of the coating thickness to the membrane thickness increases. This further improves the memory of the membrane as described in our WO 00/67668A, the entire contents of which are incorporated herein by reference.

Figure 15:
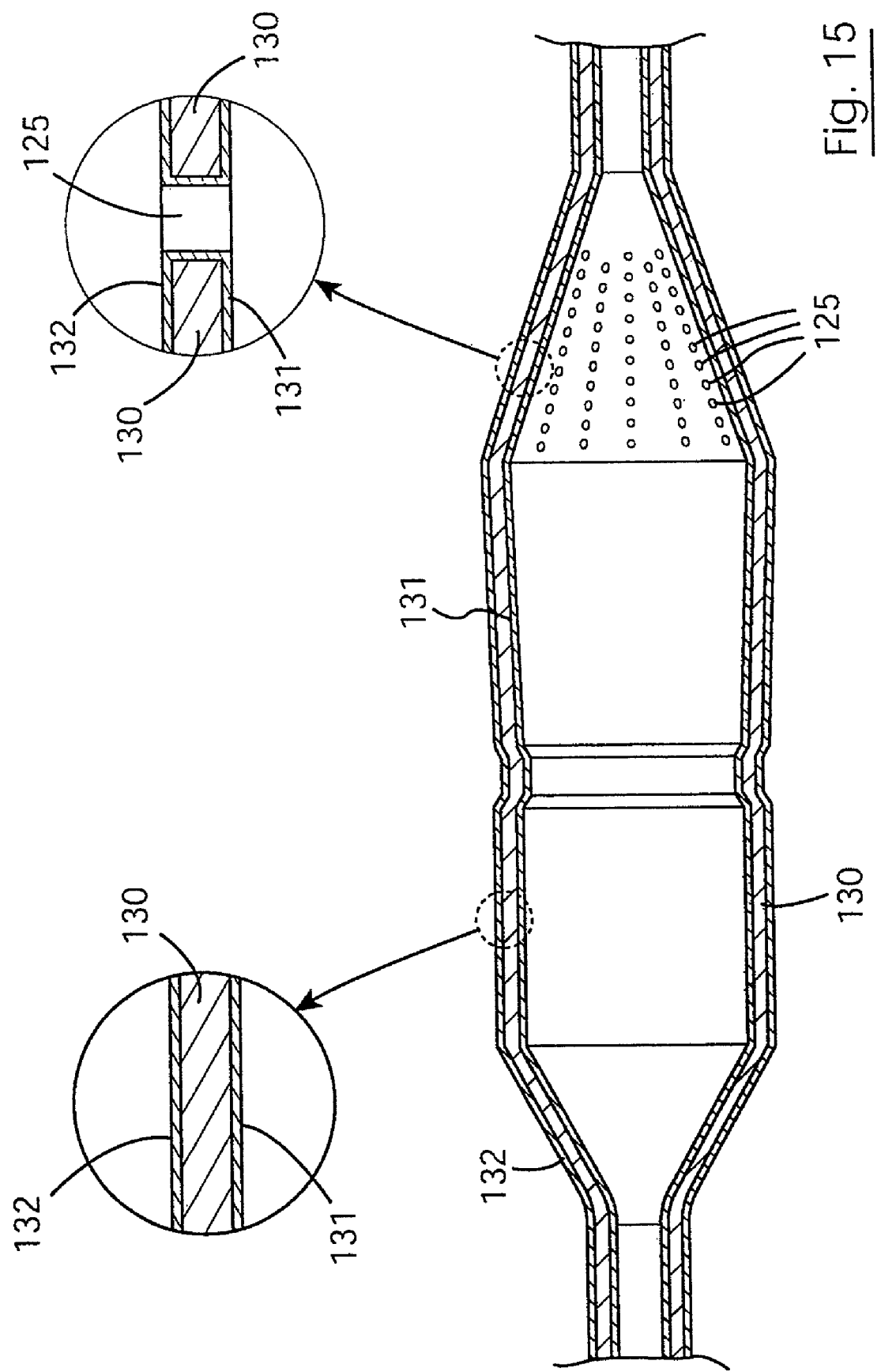
FIG. 15 is a cross sectional view of the filter body with inner and outer coatings.
Figure 16:
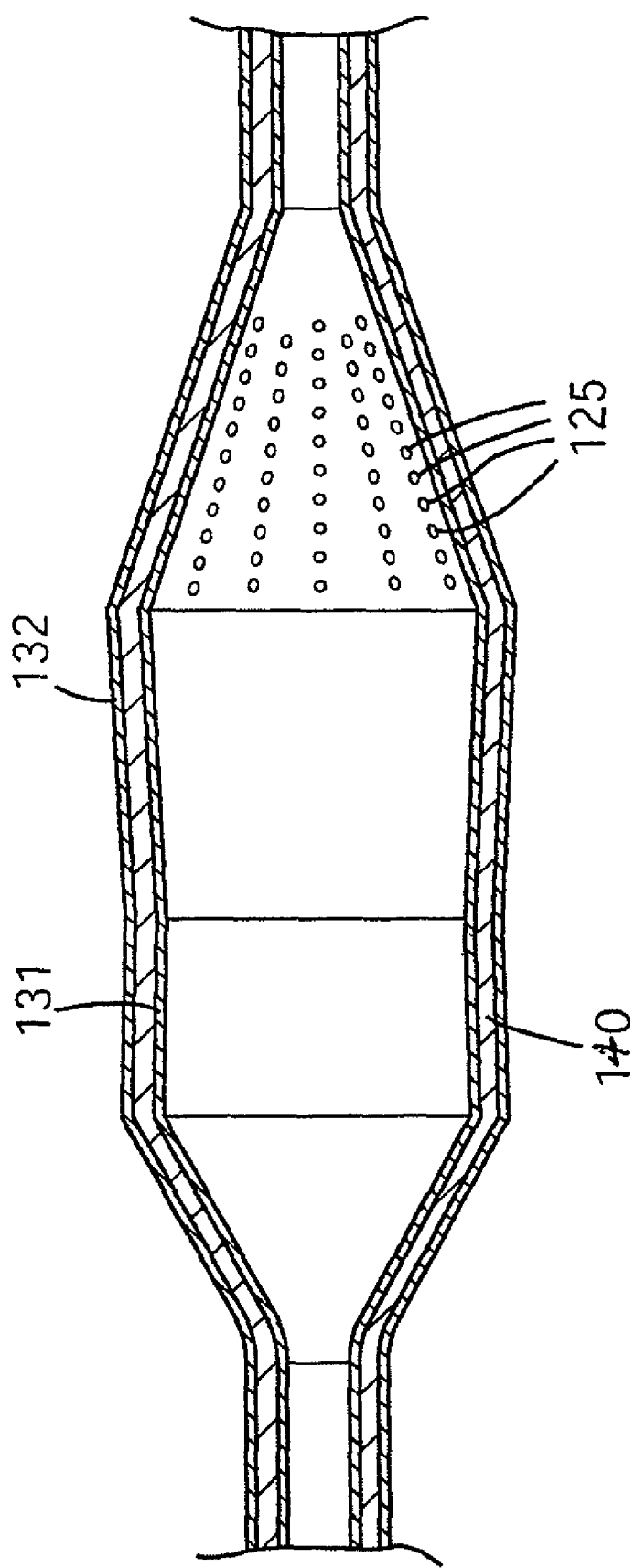
FIG. 16 is a cross sectional view of another filter body according to the invention.

Referring to FIG. 15 there is illustrated a filter body of laminate construction comprising a membrane 130 as described above with an inner hydrophilic coating 131 and an outer hydrophilic coating 132. The filter membrane 140 of FIG. 16 is shorter than the filter membrane of FIG. 15 and is thus partially suitable for renal applications.

In terms of the materials of this invention the level of stored orientation is most critical. In the invention the level of stored orientation is maximized so as to achieve the optimum balance of strength and flexibility.

The storage of orientations in the material is a complex materials and process related phenomenon. The orientations may be molecular or crystal in character. In general orientations are induced at temperatures well above the $T_g$ of the material and are stored best at temperatures below the $T_g$ of the material. Orientations can also be stored through strain crystallization processes. This involves providing the appropriate level of thermal energy to the material while it is in the stretched configuration to facilitate crystallization of the material. This process is especially important in crystalline material or in two phase materials. Polyurethanes are important two phase materials where there is a crystallizing hard phase and a soft phase.

When sufficient thermal energy is provided stored orientations will relax. The storage of orientation is characterized per this invention by measuring the linear shrinkage of the membrane at temperatures well in excess of the $T_g$ of the material. The membrane is placed in an oven at the material relaxation temperature and the level of shrinkage is measured in the two axis of the surface. The level of shrinkage provides a measure of the level of orientation in the sample. The level of stored orientation is calculated as follows:

$$\text{Axial Orientation} = \frac{(\text{Starting Length} - \text{Relaxed Length})}{\text{Relaxed Length}} \times 100\%$$

$$\text{Circumferential Orientation} = \frac{(\text{Starting Circumference} - \text{Relaxed Circumference}) \times 100}{\text{Relaxed Circumference}}$$

$$\text{Stored Bi-axial Orientation} = \frac{(\text{Starting Area} - \text{Relaxed Area}) \times 100\%}{\text{Relaxed Area}}$$

While it is not a primary purpose of the invention to generate circumferential orientation low levels of circumferential orientation has a stabilizing effect on the filter. A filter which has high levels of axial orientation and no circumferential orientation would be prone to longitudinal tearing even when loaded in the axial direction. This is not desirable. However due to the nature of the process some circumferential orientations will inevitably be present. Where high inflation ratios are used the level of circumferential orientation will be increased. This can present a problem in that high levels of circumferential orientation reduce the levels of axial orientation. Axial and circumferential orientations are competitive phenomenon. Thus where high inflation ratios are used it is an object of the current invention to minimize the level of circumferential orientation. This can be achieved by a number of techniques.

Use the largest initial tubing OD possible. This minimizes the blow ratio which reduces the level of circumferential orientation. Techniques have been described earlier in the invention, which allow large diameter necks to be reduced post stretch blow moulding.

Circumferential orientations can be converted into axial orientations if the axial stretch occurs after the circumferential stretch. This principle can be used during the stretch blow process to control the level of axial orientation.

A process which starts with a tubing that is highly oriented in the circumferential direction (shrink tubing), and is shrunk onto a core while being stretched axially provides a method of turning high initial levels of axial orientations into high levels of axial orientation at the end of the process.

In a preferred embodiment the membrane is manufactured in a process consisting of some or a combination of the following steps: 1. Tube extrusion, 2. Stretch Blow moulding, 3. Filling/Moulding/Casting, 4. Laser Machining, 5. Core Removal, 6. Forming, 7. Neck Swaging, 8. Assembly, 9. Surface Priming/Activation, 10. Coating.

In another embodiment the membrane is a laminate construction. The laminate construction may consist of soft layers and hard layers. The hard layer has the advantage that it has an ability to retain orientation. The soft layer has excellent memory properties.

The manufacturing process for the construction of the filter membranes of this invention consists of the following steps:

Tube Extrusion:

A thermoplastic polymer is extruded into concentric tubing. The tubing may be extruded as a homogenous material, as a material with reinforcing fillers, as a material with radiopacifying fillers, as a multi-layer co-extruded tubing or as a combination of the above. Very tight control of tolerances is critical at this stage. Tight control may be achieved by extruding the tubing onto a solid mandrel and removing the mandrel at the end of the step. Additional control may be achieved by employing a gear pump extrusion system.

Stretch Blow Moulding:

The tubing is placed in a heated die, and is inflated and stretched. The inflation process pushes the softened material to the wall of the die and introduces circumferential orientation into the material. The axial stretch process introduces axial orientation into the membrane. The stretch and blow processes may be carried out in stages, independently or simultaneously. The temperature at which the materials are oriented and formed varies depending on the polymer. However, typically the stretch and blow temperatures are above the $T_g$ of the material or one of its phases and below the $T_m$ of the material.

Conditioning:

The membrane material is temperature conditioned to stabilize the orientations. This is normally carried out at a temperature greater than the stretching temperature and in the region of the crystallization temperature ($T_c$).

Filling:

The formed membrane is then filled with a soluble filler polymer. The soluble filler material has the characteristic that it is soluble in a solvent to which the membrane material is resistant. The preferred filler material per this invention is polyethylene glycol (PEG), and the preferred solvent is a combination of water and a surfactant. Preferably the surfactant is a mixture of a nonionic surfactant and an anionic surfactant. Preferably the content of nonionic surfactant is 5-15% and the content of anionic surfactant is 15-30%. The remainder is water.

Laser Machining:

The filled membrane then has at least one large hole machined through the blood inlet end of the membrane and has multiple small holes machined through the blood outlet end of the membrane. The PEG material provides the membrane with structure during handling, it ensures that the membrane can only occupy one configuration and it prevents undesirable scorching.

Core Removal:

The filler material is then dissolved in water-surfactant solution to leave the finished membrane. The solution details are described above. Preferably the solution is warm during the cone removal process. However, the solution temperature should be kept below the $T_g$ of the membrane.

Profiling:

As discussed earlier it is desirable to carry out the stretch blow moulding step using relatively large diameter tubing. This ensures that a high level of axial orientation is possible and the membrane can be fabricated with exceptionally thin wall thicknesses.

Prior to the assembly of the membrane and the Nitinol support it is necessary to reduce the profile of the large diameter necks. This can be achieved using a number of techniques as follow:

The neck may be swaged to reduce its profile.

A thin walled metallic marker band may be placed over the neck and both elements swaged together. This is a particularly desirable approach as a low profile is achieved and the marker band is more radiopaque and thus highlights the extremities of the filter assembly.

The neck may have one or more longitudinal slots cut along its length. These slots reduce the effective circumference of the neck. The neck may thus be bonded to the Polyamide shaft and Nitinol support at a lower profile.

The neck may be stretched or post formed to reduce its OD.

Assembly:

The inner tube, the support structure and the filter membrane are assembled using standard techniques.

Surface Priming/Activation:

The surface of the filter assembly is prepared for coating by one or a combination of the following methods:

Solvent activation

Plasma treatment

Coating with a surface primer

UV treatment

Other standard surface activation methods

Coating:

The filter assembly is coated with a hydrophilic coating. The performance of the coating may be assessed by water contact angle analysis. Preferably the contact angle is less than 40°, more preferably less than 30° and more, preferably less than 20°.

The filter body material may also be a polyurethane or PEBAX based material. There are a series of commercially available polyurethane materials that may be suitable. These are typically based on polyether or polyester or polycarbonate or silicone macroglycols together with diisocyanate and a diol or diamine or alkanolamine or water chain extender. Examples of these are described in EP-A-461,375 and U.S. Pat. No. 5,621,065. In addition, polyurethane elastomers manufactured from polycarbonate polyols as described in U.S. Pat. No. 5,254,622 (Szycher) are also suitable.

The filter material may also be 3 polycarbonate urethane, an example of which may be prepared by reaction of an isocyanate, a chain extender and a polycarbonate copolymer polyo of alkyl carbonates. This material is described in our WO 9924084 A.

In another embodiment the membrane material is selected for its softness and recoverability. The membrane is then processed in a manner that leads to a high level of orientation. This allows the fabrication of a membrane that is soft but very strong. The high strength of the material allows the membrane to be fabricated in a very thin wall thickness. Polyurethane's are the preferred material for this embodiment. Materials of this embodiment will have hardness values from 80 A to 55 D. Suitable materials are listed in the table below.

| Manufacturer | Grade | Shore Hardness | Ultimate Tensile Strength MPa.* |
| --- | --- | --- | --- |
| Dow Chemical | Pellethane 2363-55DE | 53D | 45 |
| Thermedics Inc. | Tecothane TT 1055D | 54D | 66.2 |

High strength polyurethanes with hardnesses in excess of 55 D are suitable alternatives to PET in the manufacture of high modulus, flexible membranes. These polyurethanes have a better ability to store orientations than the softer grades and their strength properties can thus be amplified to a greater extent. The materials have ultimate tensile strength values as outlined in table I below.

| Manufacturer | Grade | Shore Hardness | Ultimate Tensile Strength MPa.* |
|---|---|---|---|
| Dow Chemical | Pellethane 2363-65DE | 62D | 47 |
| Thermedics Inc. | Tecothane TT 1065D | 64D | 69.0 |
| | Tecoflex EG-65D | 60D | 57.2 |

*Figures as quoted by manufacturer

The polymeric oriented filter membranes of the invention offer very considerable advantages as follows:

Delivery Profile

The wall thickness of the filter membrane contributes significantly to the delivery profile of the filter assembly. The profile of the filter assembly can thereby be minimized. The required wall thickness of the membrane is primarily determined by the need for robustness. The filter assembly has sufficient strength to be retrieved into a retrieval catheter with its trapped embolic load. The forces of retrieval depend on the size of the embolic load. Failure of the filter membrane during the retrieval step would likely result in the liberation of a bolus of embolic material. This is a critical failure and could result in serious patient injury or death. The incorporation of high levels of axial orientations allows the profile of the device to be significantly reduced. The use of a 3-dimensional support structure provides excellent vessel apposition as described in our WO 00/67669A.

Strength

Reducing the profile of the device makes it easier to pack the material of the device into a retrieval system. This has the effect of reducing the retrieval forces. This reduces the safety threshold for membrane strength. The additional strength achieved by inducing orientations in the membrane increases the safety of the device. The processing of the membrane in a fashion which yields in excess of 25% axial and circumferential orientation increases the strength of the resulting membrane. Strengths as high as 70-80 MPa are achievable using the soft polyurethanes described, while strengths in excess of 200 MPa and 300 MPa are achievable using PET.

Atraumatic

Atraumatic materials are desirable for filter membranes because they are in direct contact with the vessel wall. Usually this is achieved by using soft materials. However, it is the local pressure that the membrane applies to the wall of the vessel that determines the level of trauma. In this invention vessel trauma is minimized by using very thin walled, high strength and flexible membrane materials. The materials are optimized for their strength to hardness ratio. However the use of axially and biaxially orientated membranes allows the use of low relative hardness materials while still achieving desirable robustness and low profile properties.

Vessel Apposition

It is desirable that filter membranes have good apposition to the wall of the vessel. Good vessel apposition is achieved by using an inner 3-D metallic support structure. The metallic support structure gently presses the membrane against the wall while the membrane flexibility prevents vessel trauma.

Filter Membrane Memory

The membranes of some embodiments of this invention use relatively soft materials with high levels of orientation. This means that the strength is maximized while the wall thickness of the membranes is minimized. This is achieved without significantly impacting the flexural modulus of the membrane. The memory properties of membranes of this invention are superior to non-oriented membranes. This is because it is possible using the invention to produce membranes with high strength but reduced wall thickness. This reduced wall thickness means that a hydrophilic coating will represent a more significantly proportion of the total wall thickness. This means that the hydrophilic coating has a more profound affect on the memory properties of the filter.

The filter member of the invention provides apposition to the vessel into which it is placed. Vessel apposition ensures that the blood flows through the filter rather than around the periphery of the filter. The filter also applies a low pressure to the vessel surface. Such low pressure ensures that the filter is non-traumatic to the vessel. The membrane can also be wrapped to a small diameter delivery configuration. This small diameter delivery configuration facilitates the crossing of the diseased area. The filter assembly is flexible in the wrapped configuration (trackable) which makes lesion crossing easier. The filter is sufficiently robust to withstand loading into a delivery configuration, to withstand the forces of deployment and to withstand the forces of retrieval of the assembly.

EXAMPLE 1

An extrusion grade PET with a starting tensile strength of 12,000 psi is extruded into a tube. The tubing OD was approximately 0.95 mm. The tube is cut into lengths of greater than 75 mm.

A stretch blow mould was machined from brass. The mould had a neck ID was 0.98 mm. The maximum body dimension of the mould was 4.20 mm. The length of the mould was 13.84 mm. The mould contained a circumferential groove in its mod section. The shape of the mould was consistent with the shape of the membrane blank 90 of FIG. 7.

The mould was mounted onto a stretch blow-moulding machine. The mould is heated in a controlled fashion. The tubing is placed inside the mould with its ends projecting out either side of the mould. The ends of the tubing were gripped while maintaining the ability to pressurize the tube lumen pneumatically.

When the tubing reached an equilibrium temperature with the mould the tubing was stretched in the axial direction. Inflation of the lumen stretched the filter in the circumferential direction. The level of circumferential orientation is determined by the blow ratio which in this case was approximately 4.3:1.

The stretch ratio in the axial direction is more difficult to calculate due to the fact that the temperature of the tubing is different at different points along the gauge length.

The membrane was stabilized by increasing the mould temperature for a short period. The mould was then cooled below the glass transition temperature (65° C.), thus freezing in the induced orientation of the PET membrane. The formed membrane blank 90 (FIG. 7) was removed from the mould. At this stage the ends 91,92 of the tubing were heat sealed under a slight positive pressure. This prevents further shrinkage and/or crinkling of the membrane while it awaits further processing.

Filling of Membranes

The heat-sealed PET filter membrane neck sections were trimmed-off and the filter blank 90 was mounted onto a dispensing tip 95 (supplied by EFD) with the distal end of the membrane facing luer 96. The tip 95 was modified by introducing two stepped slots 97 midway along the hypotube section of the dispensing tip. The two slots 97 are at 180° to each other.

A polyurethane collar 99 was then slid onto the end of the dispensing tip to prevent the filter membrane from sliding-off and secondly to assure that the mid-section of the filter body blank 90 is located at the slotted section of the dispensing tip 95. The slots 97 in the hypotube provide apertures for the filling material to flow out and fill the membrane. The dispensing tip has a luer fitting 96 which provides an easy interface with the filling system.

The material used for filling the filler membrane blank 90 polyethylene glycol (molecular weight=1500) from Sigma Aldrich. Polyethylene glycol flakes (PEG) were placed in a heated dispensing chamber and heated to 51° C., the filling material was in a molten state and the temperature of the liquid PEG had stabilized to 51° C., the membrane-slotted hypotube assembly was fitted onto the heated dispensing chamber. The filling time was 2.5 seconds. The dispensing pressure for the molten PEG was 1.20 bar. Filling material 110 is injected through the dispensing tip 95, exiting through the slots 97 to fill the membrane blank 90 (FIGS. 8 to 10).

A water bath was placed directly underneath the filling barrel. This water bath was connected to a water chiller that continuously replenished the water of the bath at a controlled temperature of 15° C. After filling was complete the filter and filler material were immersed into a cooling bath for a period of 47 seconds.

Laser Machining

The filled filter membrane blank 90 was then laser machined as illustrated in FIGS. 11 and 12. An Eximer laser 120 operating at a wavelength of 248 mm was used. The energy was delivered in a pulsed format. The machining area was blanketed with a continuous stream of nitrogen to prevent melting or scorching. Two large holes 122 were machined, radially opposite, on the proximal end of the membrane and 290 holes 125 were machined into the distal end of the membrane blank 90. The proximal holes 122 were machined such that a large embolus would pass through the opening and both holes were positioned radially opposing one another. The distal holes were machined to a nominal diameter of 140 microns. No material scorching was observed.

Core Removal

The PEG filling material 110 was then removed from inside the membrane. This was achieved by dissolving the PEG material in a solvent system in a bath 130. The PEG material was dissolved in a number of steps:

The bulk of the material was removed with a HPLC grade water wash. This was carried out by immerging the filter membranes in water at 50° C. for 5 minutes.

The filter membranes were flushed with 10 ml HPLC grade water using a syringe.

An extraction step was employed to remove all remaining PEG. The extraction solvent was a mixture of HPLC grade water and 0.5% surfactant. The surfactant was composed of <5% amphoteric surfactants, 5-15% non-ionic surfactants and 15-30% ionic surfactants in a water matrix. Approximately 400 ml of extraction solvent was used per filter membrane. The extraction solvent was maintained at a temperature of 50° C. during the extraction. The membranes were removed after 1 hour.

Each filter membrane was flushed with 10 mm of HPLC grade water to remove any residues of the extraction solution.

The filter membranes were washed in HPLC grade water for 1 hour at 50° C. Fifty filters were washed in 1000 ml water.

The filter membranes were dried in an oven at 45° C. for 2 hours.

Results

Figure 14:
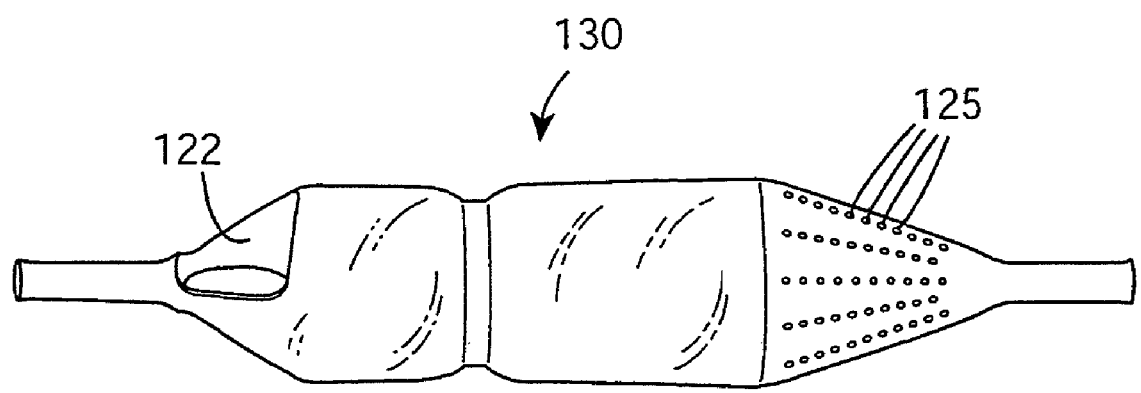
FIG. 14 is a side view of a filter body according to the invention.

Samples of membrane filters 130 (FIG. 14) processed as described above were evaluated for stored axial orientation and ultimate tensile strength. The ultimate tensile strength was measures in the area of the proximal holes. It is an objective of this invention to provide the largest proximal holes possible. The size of the proximal holes is largely determined by the axial tensile strength of the material between the holes. This web area is the weakest area of the filter.

The body lengths of four membrane filters were measured using a toolmakers microscope. The membranes were then placed into a fan-assisted oven with a preheated temperature setting of 220° C. The membranes were removed after 3 hours and the body lengths were measured. The stored axial orientation was calculated as described above. The average level of stored axial orientation was 34.5%.

Samples of membranes from the same batch were evaluated for ultimate axial tensile strength. The strength measurements were made in the web region. The samples were prepared by cutting one web so as to focus the tensile load on the other web. The width and thickness of the web was measured. The cross sectional area of the web was calculated based on these measurements. A Zwick Z0D5 model tensile test machine was used with a 500N load cell. The instrument was set to record the maximum load. The samples were gripped using toolmakers clamps and the toolmakers clamps were mounted to the machine base and cross-head. A fine grade emery cloth was used to ensure a positive grip. After sample mounting the cross head distance was zeroed and the test started. A test speed of 50 mm/min was used. The samples were tested at ambient temperature. The results demonstrated ultimate tensile strength values in excess of 40,000 psi. This represents an increase of 330% in the tensile strength of the material arising from the invention. These strength characteristics allow membranes with exceptional advantages to be achieved.

Figure 18:
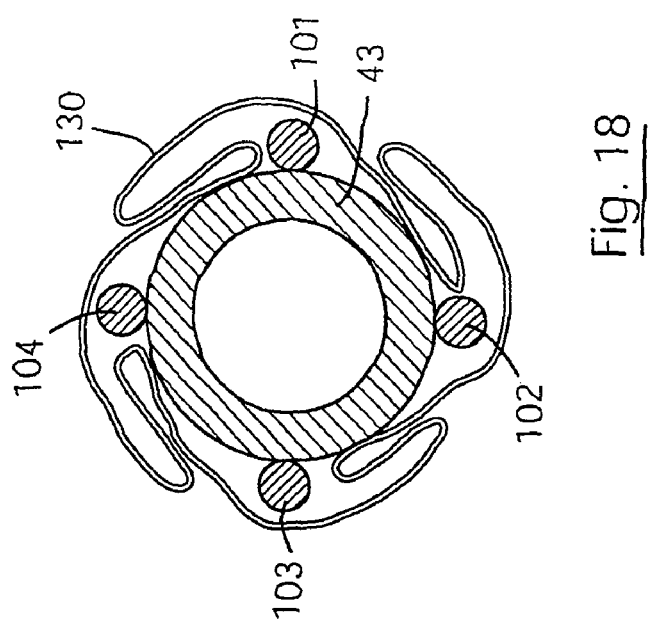
FIG. 18 is a cross sectional view of the filter body of FIG. 17 in a collapsed configuration.
Figure 17:
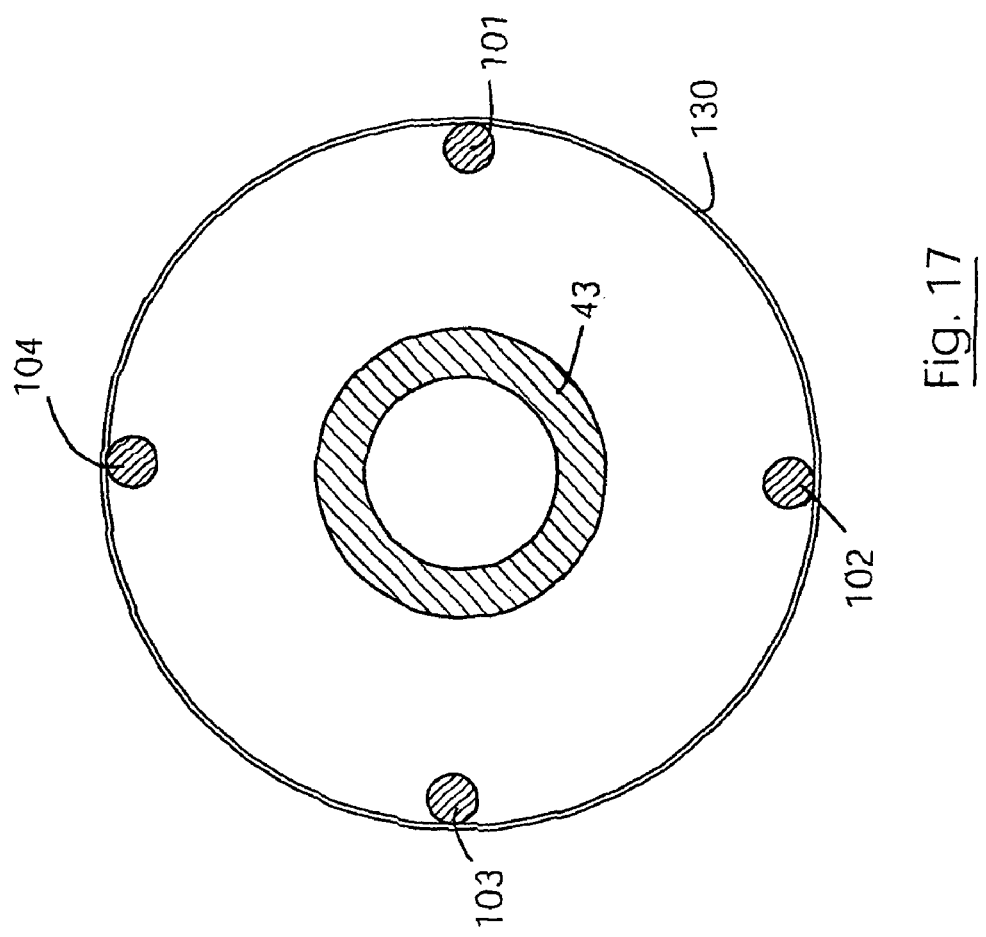
FIG. 17 is a transverse cross sectional view of the filter body of FIG. 15 and associated supports and sleeve.

The use of orientation in the filter membrane has a number of very significant user advantages as described above. As it is possible to use a much thinner membrane the wrapping efficiency is increased and it is possible to achieve greatly reduced delivery profiles. Furthermore with reference to FIG. 18 it is possible with this invention to provide filler systems that are pre-wrapped. This eliminates a cumbersome wrapping operation in the catherization laboratory. This has not been possible to date with membrane filters due to issues of air embolization. It is an essential element of filter design that all air is removed prior to deliver to the deployment site. Oriented thin walled membranes that do not possess memory have the advantage that they can form very tight radius of curvature at crease locations. This allows the filter to be pre-wrapped in a very ordered configuration. The highly ordered configuration of the type shown in FIG. 18 ensures that there are very few void spaces and that all fluid gaps are of the same dimension. When received by the user a simple syringe flush is all that is required to eliminate air emboli. FIG. 18 describes a wrapping configuration with 4 points of folding. However any number of folds form two or greater could be used. These are very compelling advantages of this invention and greatly simplify the use of filtration products.

The invention is not limited to the embodiments hereinbefore described which may be varied in both construction and detail.

The invention claimed is:

1. A collapsible filter element for a transcatheter embolic protection device, the filter element comprising:
   a collapsible filter body which is movable between a collapsed stored position for movement through a vascular system and an expanded position for extension across a blood vessel such that blood passing through the blood vessel is delivered through the filter element;
   a proximal inlet portion of the filter body having one or more inlet openings sized to allow blood and embolic material enter the filter body;
   a distal outlet portion of the filter body having a plurality of outlet openings to allow through-passage of blood, but to retain embolic material within the filter body;
   the filter element being pre-wrapped in a ordered configuration which can eliminate air emboli in the loading process and the filter body comprising a thin membrane.

2. A filter element as claimed in claim 1 comprising a wrapping configuration with 4 points of folding.

3. A filter element as claimed in claim 1 comprising a collapsible support frame, the support frame being movable between a collapsed position for movement through the vascular system and an extended outwardly projecting position to support the filter body in the expanded position.

4. A filter element as claimed in claim 3 wherein the filter body is independent of the support frame.

5. A filter element as claimed in claim 3 wherein the frame comprises a plurality of engagement segments, the engagement segments being spaced-apart longitudinally and transversely when the filter is in the deployed expanded configuration to urge the filter body into apposition with the vessel wall.

6. A filter element as claimed in claim 5 wherein the engagement segments define at least one at least partially substantially helical engagement track.

7. A filter element as claimed in claim 1 wherein the thin membrane comprises a polyamide having stored orientations.

8. A filter element as claimed in claim 7 wherein the filter body has a stored axial orientation in excess of 15%.

9. A filter element as claimed in claim 7 wherein the filter body has a stored axial orientation in excess of 20%.

10. A filter element as claimed in claim 7 wherein the filter body has a stored axial orientation in excess of 30%.

11. A filter element as claimed in claim 7 wherein the filter body has a stored axial orientation in excess of 40%.

12. A filter element as claimed in claim 7 wherein the ultimate tensile strength of the oriented polyamide of the filter body is at least 15,000 psi (103.425 MPa).

13. A filter element as claimed in claim 12 wherein the ultimate tensile strength is at least 25,000 psi (172.375 MPa).

14. A filter element as claimed in claim 12 wherein the ultimate tensile strength is at least 35,000 psi (241.325 MPa).

15. A filter element as claimed in claim 12 wherein the ultimate tensile strength is at least 40,000 psi (275.8 MPa).

16. A filter element as claimed in claim 7 wherein the polyamide of the filter body is oriented at a temperature below the glass transition temperature of the material.

17. A filter element as claimed in claim 7 wherein the polyamide of the filter body is oriented by stretch blow moulding.

18. A filter element as claimed in claim 1 wherein the filter body comprises a proximal body section, a distal body section and an intermediate body section interconnecting the proximal and distal body sections.

19. A filter element as claimed in claim 7 wherein the polyamide is biaxially oriented.

20. A filter element as claimed in claim 19 wherein the filter body has a stored biaxial of orientation in excess of 30%.

21. A filter element as claimed in claim 19 wherein the filter body has a stored biaxial of orientation in excess of 60%.

22. A filter element as claimed in claim 19 wherein the filter body has a stored biaxial orientation in excess of 80%.

23. A filter element as claimed in claim 19 wherein the filter body has a stored biaxial of orientation of 100%.

* * * * *